(12) United States Patent
Vukicevic et al.

(10) Patent No.: US 8,197,840 B2
(45) Date of Patent: Jun. 12, 2012

(54) WHOLE BLOOD-DERIVED COAGULUM DEVICE FOR TREATING BONE DEFECTS

(75) Inventors: Slobodan Vukicevic, Zagreb (HR); Lovorka Grgurevic, Zagreb (HR); Hermann Oppermann, Medway, MA (US)

(73) Assignee: Genera Istrazivanja d.o.o., Kalinovica (HR)

( * ) Notice: Subject to any disclaimer, the term of this patent is extended or adjusted under 35 U.S.C. 154(b) by 487 days.

(21) Appl. No.: 12/309,512

(22) PCT Filed: Jul. 23, 2007

(86) PCT No.: PCT/US2007/016601
§ 371 (c)(1),
(2), (4) Date: Jan. 21, 2009

(87) PCT Pub. No.: WO2008/011192
PCT Pub. Date: Jan. 24, 2008

(65) Prior Publication Data
US 2009/0317438 A1  Dec. 24, 2009

Related U.S. Application Data

(60) Provisional application No. 60/832,732, filed on Jul. 21, 2006.

(51) Int. Cl.
*A61F 2/00* (2006.01)
(52) U.S. Cl. .................................................. 424/426
(58) Field of Classification Search .................. None
See application file for complete search history.

(56) References Cited

U.S. PATENT DOCUMENTS

| | | | |
|---|---|---|---|
| 4,968,590 A | 11/1990 | Kuberasampath et al. | |
| 5,011,691 A | 4/1991 | Oppermann et al. | |
| 5,171,579 A | 12/1992 | Ron et al. | |
| 5,385,887 A | 1/1995 | Yim et al. | |
| 5,496,552 A | 3/1996 | Kuberasampath et al. | |
| 5,674,844 A | 10/1997 | Kuberasampath et al. | |
| 6,117,425 A * | 9/2000 | MacPhee et al. | 424/94.64 |
| 6,333,312 B1 | 12/2001 | Kuberasampath et al. | |
| 2007/0014780 A1 * | 1/2007 | Woolverton | 424/94.64 |

FOREIGN PATENT DOCUMENTS

| | | |
|---|---|---|
| CA | 2 436 162 A1 | 8/2002 |
| DE | 198 05 673 A1 | 8/1999 |
| WO | WO 96/39170 A1 | 12/1996 |

OTHER PUBLICATIONS

Applicant's Response to the Written Opinion as filed for international application No. PCT/US2007/016601 on Jan. 6, 2009.
International Search Report for international application No. PCT/US2007/016601 (Oct. 7, 2008).
Written Opinion of the International Searching Authority for international application No. PCT/US2007/016601 (Oct. 7, 2008).

Asahina et al., Human Osteogenic Protein-1 Induces Chondroblastic, Osteoblastic and/or Adipocytic Differentiation of Clonal Murine Target Cells, *Exp. Cell. Res.*, 222: 38-47 (1996).
Griffith et al., Three-dimensional structure of recombinant human osteogenic protein 1: Structural paradigm for the transforming growth factor βsuperfamily, *Proc. Natl. Acad. Sci. USA*, 93: 878-883 (1996).
Hoffmann et al., Perspectives in the biological function, the technical and therapeutic application of bone morphogenetic proteins, *Appl. Microbiol. Biotechnol.*, 57: 294-308 (2001).
Jones et al., Osteogenic Protein-1 (OP-1) Expression and Processing in Chinese Hamster Ovary Cells: Isolation of a Soluble Complex Containing the Mature and Pro-Domains of OP-1, *Growth Factors*, 11: 215-225 (1994).
Kim et al., PBMP on Healing of Bone Defect, *Yonsei Medical Journal*, 33(1): 54-63 (1992).
Reddi, J., Bone Morphogenetic Proteins: From Basic Science to Clinical Applications, *J. Bone Joint. Surg.*, 83-A (Supp. 1): S1-1-S1-6 (2001).
Sampath et al., Dissociative extraction and reconstitution of extracellular matrix components involved in local bone differentiation, *Proc. Natl. Acad. Sci. USA*, 78(12): 7599-7603 (1981).
Sampath et al., Isolation of osteogenin, an extracellular matrix-associated, bone-inductive protein, by heparin affinity chromatography, *Proc. Natl. Acad. Sci. USA*, 84: 7109-7113 (1987).
Urist et al., Human Bone Morphogenetic Protein (hBMP)[1] (41630), *Proc. Soc. Exp. Biol. Med.*, 173: 194-199 (1983).
Urist et al., Purification of bovine bone morphogenetic protein by hydroxyapatite chromatography, *Proc. Natl. Acad. Sci. USA*, 81: 371-375 (1984).
Vukicevic et al., Osteogenic Protein-1 (Bone Morphogenetic Protein-7) Reduces Severity of Injury After Ischemic Acute Renal Failure in Rat, *J. Clin. Invest.*, 102: 202-214 (1998).
Wang et al., Recombinant human bone morphogenetic protein induces bone formation, *Proc. Natl. Acad. Sci. USA*, 87: 2220-2224 (1990).
Wozney et al., Novel Regulators of Bone Formation: Molecular Clones and Activities, *Science*, 242: 1528-1534 (1988).
"c. chloride" In Grant & Hackh's Chemical Dictionary, Fifth Edition (Grant and Grant, eds.) (McGraw-Hill Book Company, New York, 1987), p. 105.
"c. s. sesquihydrate CaSO4•1/2 H2O" In Grant & Hackh's Chemical Dictionary, Fifth Edition (Grant and Grant, eds.) (McGraw-Hill Book Company, New York, 1987), p. 107.
"calcium chloride", In Oxford Dictionary of Chemistry, Sixth Edition, (Daintith, ed.) (Oxford University Press, Oxford, 2008), p. 93.
"calcium sulphate", In Oxford Dictionary of Chemistry, Sixth Edition, (Daintith, ed.) (Oxford University Press, Oxford, 2008), pp. 94-95.
Chen et al., "The Fusion Rate of Calcium Sulfate With Local Autograft Bone Compared With Autologous Iliac Bone Graft for Instrumented Short-Segment Spinal Fusion," Spine, 30(20): 2293-2297 (Oct. 15, 2005).
Dormans et al., "Percutaneous Intramedullary Decompression, Curettage, and Grafting With Medical-Grade Calcium Sulfate Pellets for Unicameral Bone Cysts in Children: A New Minimally Invasive Technique," J. Pediatr. Orthop., 25 (6): 804-811 (Nov.-Dec. 2005).
Gillespie et al., Chemistry, second edition, (Allyn and Bacon, Inc., Boston, 1989), p. 218.
Intini et al., "Calcium Sulfate and Platelet-Rich Plasma make a novel osteoinductive biomaterial for bone regeneration," J. Translational Medicine, 5:13 (2007). article available from: http://www.translational-medicine.com/content/5/1/13.
Marušić et al., "New Bone Induction by Bone Matrix and Recombinant Human Bone Morphogenetic Protein-2 in the Mouse," Croatian Med. J., 37(4): 237-244 (1996).

* cited by examiner

*Primary Examiner* — Suzanne M Noakes
(74) *Attorney, Agent, or Firm* — Thomas R. Berka; Leon R. Yankwich; Yankwich & Associates, P.C.

(57) ABSTRACT

Whole blood-derived coagulum devices are described for use in treating bone defects.

26 Claims, 9 Drawing Sheets

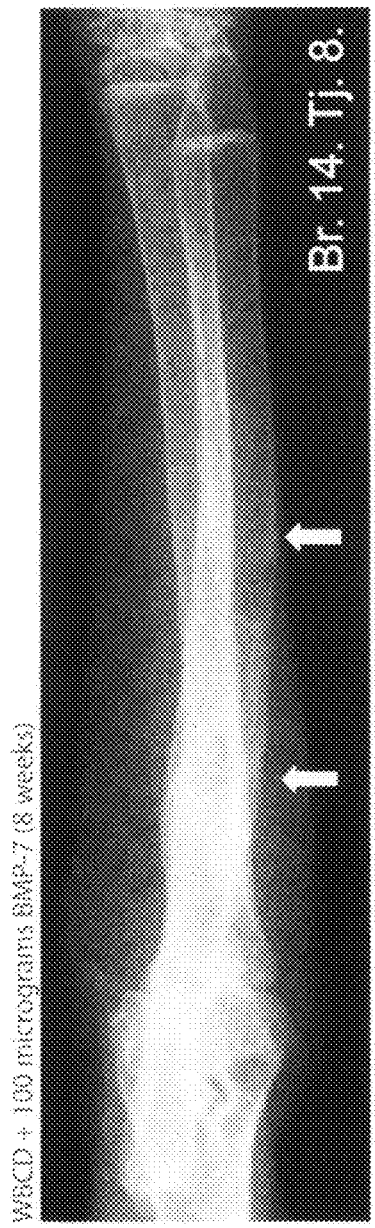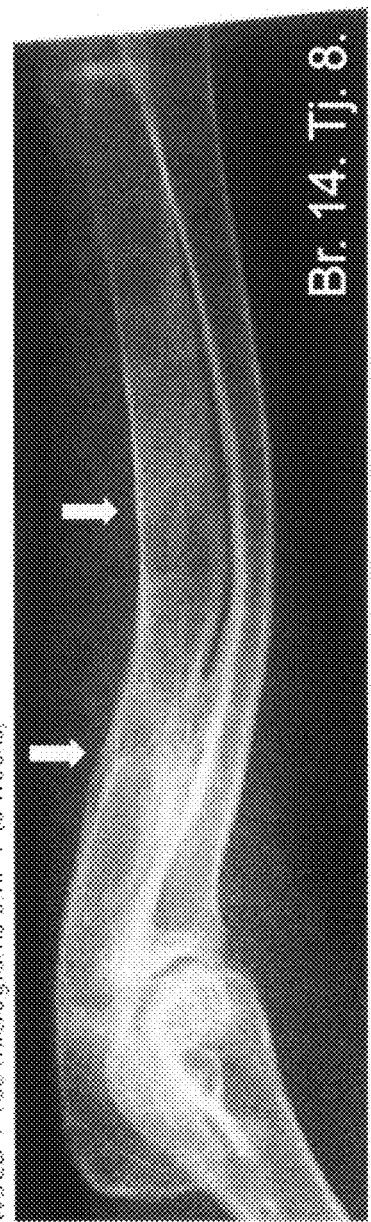
Fig. 7A
Fig. 7B

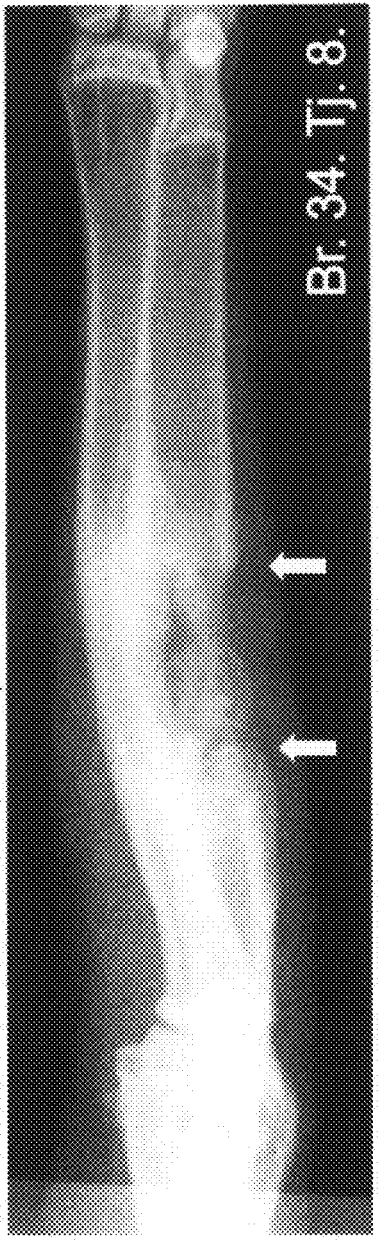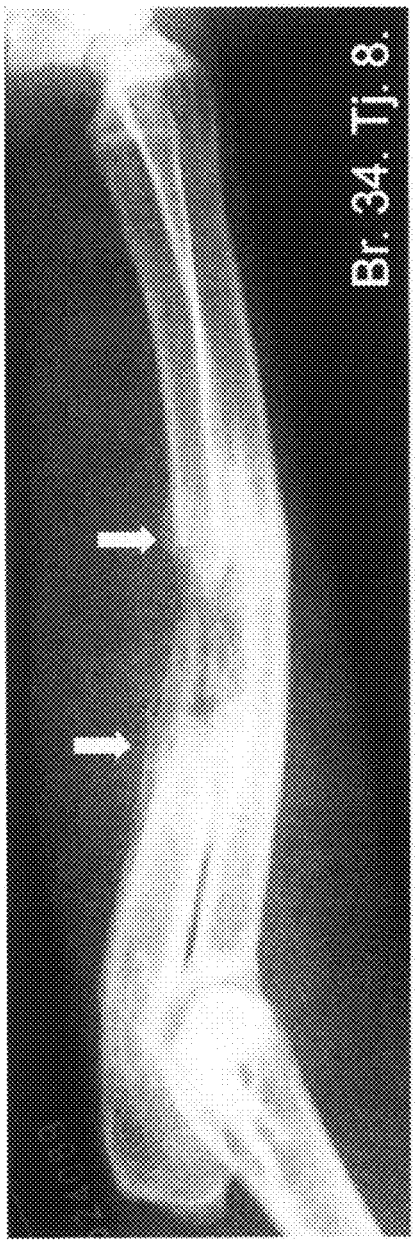
Fig. 8A
Fig. 8B

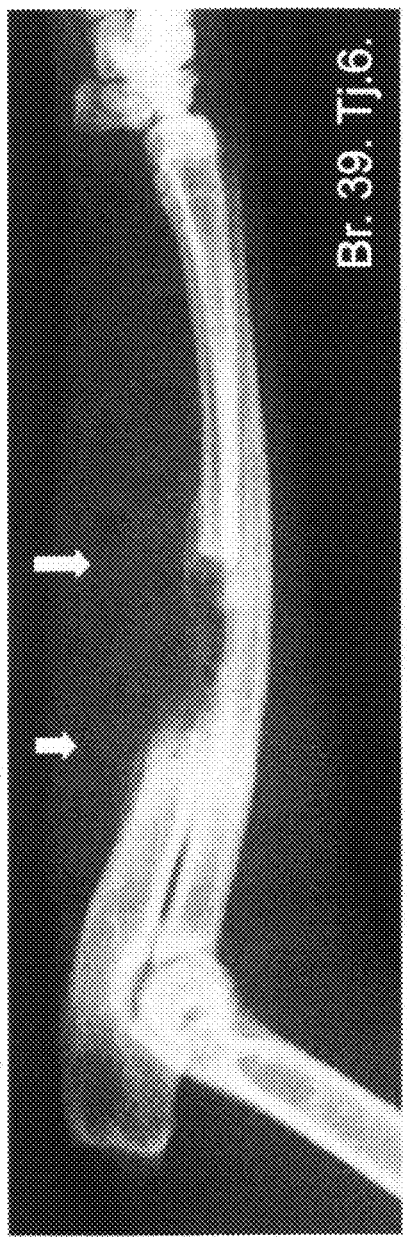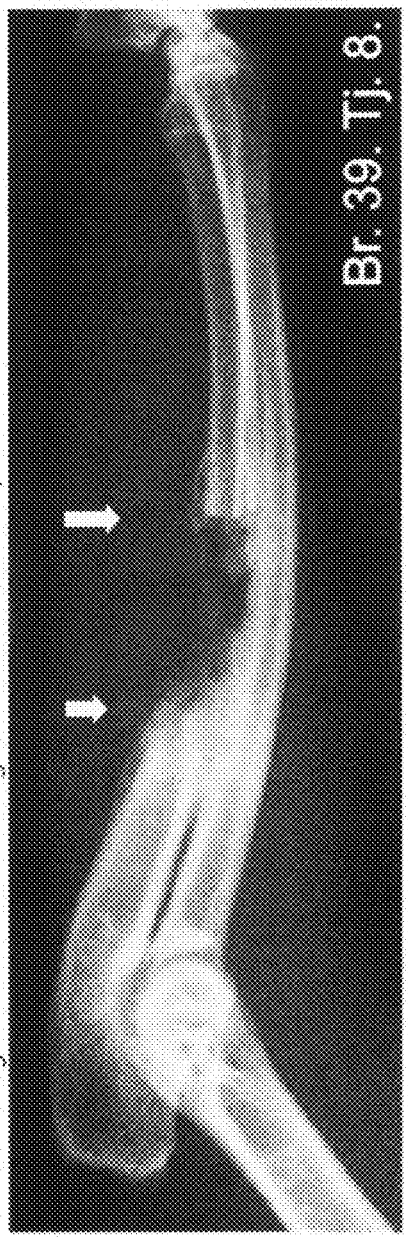

WHOLE BLOOD-DERIVED COAGULUM DEVICE FOR TREATING BONE DEFECTS

CROSS-REFERENCE TO RELATED APPLICATIONS

This application is a United States national stage filing under 35 U.S.C. §371 of international application No. PCT/US2007/016601, filed Jul. 23, 2007, designating the U.S., which claims priority to U.S. Provisional Application No. 60/832,732, filed Jul. 21, 2006.

FIELD OF THE INVENTION

This invention is in the field of treatments for bone defects. In particular, the invention provides a composition comprising a whole blood-derived coagulum derived for use in treating bone defects.

BACKGROUND

For more than 30 years, bone morphogenetic proteins ("BMPs", "morphogens", "osteoinductive proteins"), a particular subclass of the transforming growth factor-β (TGF-β) super family of proteins, have been studied to understand the role these proteins play not only in bone and cartilage formation but also in soft tissue regeneration (e.g., kidney, heart, eye) and to develop such understanding into clinically effective therapies (see, e.g., Hoffmann et al., *Appl. Microbiol. Biotechnol.*, 57: 294-308 (2001); Reddi, *J. Bone Joint Surg.*, 83-A(Supp. 1): S1-S6 (2001); U.S. Pat. Nos. 4,968,590; 5,011,691; 5,674,844; 6,333,312). In efforts to develop such BMP-based therapies to treat bone defects, it soon became clear that the preferred way to treat a bone defect would be to implant into a defect site some type of implantable matrix carrying an effective amount of a BMP.

Osteogenic BMPs applied locally support formation of new bone, cartilage, and ligaments. Currently, only a few BMP-based therapies have been approved for treating fractures. BMP-7 (OP-1) is manufactured and distributed for treatment of long bone non-union fractures by Stryker Biotech (Hopkinton, Mass., U.S.). BMP-2 is manufactured and distributed for long bone acute fractures by Wyeth Pharmaceuticals (Madison, N.J., U.S.) and for spinal fusions by Medtronic, Inc. (Minneapolis, Minn., U.S.). In each of these approved therapies, the BMP active ingredient is combined with a bovine-derived collagen matrix (bovine collagen type 1). Owing to its bovine source, the collagen must be highly purified to eliminate immunogenicity and viral contamination. Moreover, the bovine source of the collage also presents a risk of bovine spongiform encephalopathy (BSE, mad cow disease). Accordingly, the purification and processing necessary for the collagen matrix in the currently approved therapies adds considerable cost, which places these devices well beyond the means of many individuals throughout the world. Moreover, however low, the risk of BSE associated with bovine products may further limit patient acceptance of these commercially available BMP therapies. As even the purest of collagen preparations may stimulate an immune response in a patient, several new carriers have been tested, including hydroxyl apatite salts and several synthetic polymers. Such alternatives are not natural and may present their own problems, such as irritation of local tissue, immunogenicity, and unknown affects on cell and tissue physiology within a patient.

Although broad statements have been made for many decades about the possible use of many other substances as possible matrix-carriers for BMP therapies to treat bone defects, to date, only a few as those mentioned above have been developed or approved. Clearly, needs remain for effective and affordable means and methods of delivering osteogenic proteins to the sites of bone defects.

SUMMARY OF THE INVENTION

The invention solves the above problems by providing a composition described herein as a "whole blood-derived coagulum device" ("WBCD") that can serve as a carrier for an osteogenic compound to treat bone defects, including fractures and sites in a bone that are characterized by inadequate bone growth as found in various metabolic bone diseases. The WBCD described herein is a composition comprising whole blood that forms a coagulum (clot) that can be implanted or injected into a desired site of a bone defect. Coagulum alone lacks the structural integrity that is required to be applied to bone defects by injection or implantation at a desired site of a bone defect. A WBCD as described herein is a composition comprising whole blood and also a sufficient amount of a calcium ion to provide a homogeneous, cohesive, syringeable, injectable, and malleable coagulum gel.

In one embodiment, the invention provides a whole blood-derived coagulum device (WBCD) for treating a bone defect in an individual prepared by the steps comprising:
(a) combining:
(1) whole blood,
(2) an osteogenic protein,
(3) exogenously provided calcium ion, and
(4) optionally, an exogenously provided fibrin-thrombin mixture,
(b) incubating the ingredients combined in step (a) until a mechanically stable coagulum is formed,
wherein the exogenously provided calcium ion is present at a concentration that is effective to provide a homogeneous, cohesive, syringeable, injectable, and malleable coagulum gel.

Preferably, a WBCD described herein comprises autologous whole blood drawn from the individual or whole blood that has been crossmatched with the individual.

Any of a variety of osteogenic proteins may be used in a WBCD described herein. Preferably, the osteogenic protein is an osteogenic bone morphogenetic protein (BMP). More preferably, an osteogenic BMP useful in the compositions and methods described herein is selected from the group consisting of BMP-2, BMP-4, BMP-6, BMP-7, heterodimers thereof, and combinations thereof. Preferably, a BMP or other osteogenic protein is present in a WBCD described herein at a concentration in the range of 50 µg/mL to 500 µg/mL.

In another preferred embodiment, a WBCD described herein is prepared using exogenously provided calcium ion present in the range of 1 mM to 2.5 mM, inclusive. A preferred source of calcium ion is calcium chloride. A preferred range for using exogenously added calcium chloride in a WBCD is 5 mM to 15 mM, inclusive.

In a preferred embodiment, a WBCD is prepared with an exogenously provided mixture of fibrin and thrombin (optional ingredient 4, above). Fibrin-thrombin mixtures useful in a WBCD described herein may be made by simply mixing fibrin and thrombin in with the other ingredients of the WBCD. Alternatively, fibrin and thrombin may be premixed or purchased as a mixture, and the mixture then added to the other ingredients. Fibrin-thrombin mixtures useful in a WBCD include what are known in the art as "fibrin glue" or "fibrin sealant". Commercial preparations of fibrin-thrombin mixtures, fibrin glues, and fibrin sealants are readily available. The fibrin and thrombin available in the art for use in a WBCD described herein are not a source of significant immunogenicity that would normally elicit an immune response in most individuals. Preferably, the exogenously provided fibrin-thrombin mixture provides fibrin in the range of 5 mg/mL to 10 mg/mL, inclusive, and thrombin in the range of 0.5 mg/mL to 5 mg/mL. A fibrin-thrombin mixture is particularly preferred to entrap an osteogenic BMP and thereby enhance retention of the BMP in the WBCD locally in a defect site. The presence of a fibrin-thrombin mixture also enhances the consistency and other features of the WBCD. Accordingly, lower amounts of a fibrin-thrombin mixture may be used as the size of a bone defect decreases or the distance to be rebridged by new bone growth between bone ends of a defect decreases.

Incorporating an exogenously provided fibrin-thrombin mixture into a WBCD is particularly useful to entrap the osteogenic protein ingredient prior to addition of whole blood and its subsequent coagulation. Such entrapment of the osteogenic protein ingredient in a fibrin-thrombin matrix prior to coagulation increases the retention of the osteogenic protein in the WBCD in a defect site and, thereby, enhances stimulation of new bone formation in the defect site.

In another preferred embodiment, the WBCD is prepared as mentioned above, except that step (a) is carried out by preparing a first mixture by combining the exogenously provided fibrin-thrombin mixture, the exogenously provided calcium ion, and the osteogenic protein, followed by incubating the first mixture for at least 15 minutes, and thereafter adding the whole blood to the first mixture to form a second mixture, and incubating the second mixture for about 20 minutes. This embodiment entraps the osteogenic proteins in the fibrin-thrombin mixture and thereby enhances retention of the osteogenic protein in the WBCD locally at a defect site. Accordingly, this embodiment is particularly preferred for treating relatively large defects, including critical size non-union defects, where a relatively large amount of bone must grow to fill and rebridge the defect.

A WBCD as described herein may be used to treat a bone defect, including, without limitation, bone fractures and bone characterized by inadequate bone growth as occurs in various metabolic bone diseases, e.g., osteoporosis, osteopenia, and Paget's Disease.

A WBCD as described herein is preferably administered to the site of a bone defect by injection or by implantation.

A WBCD as described herein may be used immediately upon completion of its preparation to treat a bone defect in an individual or stored for future use in treating a bone defect of the individual. Preferably, a WBCD of the invention is used to treat a bone defect within about 45 minutes from the beginning of its preparation.

In another embodiment, the invention provides a kit for preparing a whole blood-derived coagulum device (WBCD) comprising:
1. a vial containing a lyophilized osteogenic BMP,
2. a buffer for reconstituting the lyophilized BMP powder,
3. a syringe for reconstituting the lyophilized BMP in the buffer,
4. a vaccutaner for collecting a patient's blood,
5. a sterile solution of 1 M $CaCl_2$,
6. a fibrin-thrombin mixture,
7. a plastic, siliconized container for mixing whole blood with the reconstituted BMP,
8. a spatula or syringe for applying WBCD to bone ends during open surgery, and
9. instructions for the preparation and use of osteogenic WBCD using autologous or crossmatched blood.

BRIEF DESCRIPTION OF THE DRAWINGS

FIGS. 7A and 7B show X-rays of a representative ulnar critical size defect in a rabbit treated with autologous blood coagulum containing BMP-7 (100 µg) (Group C in Example 8). X-rays show that the defect has been rebridged 8 weeks after surgery. Arrows indicate edges of original defect. See, Example 8, below, for details.

FIGS. 8A and 8B show X-rays of a representative ulnar critical size defect in a rabbit treated with a commercially available collage sponge to which BMP-7 (200 µg) was added (Group E in Example 8). X-rays show that the defect has been rebridged 8 weeks after surgery. Arrows indicate edges of original defect. See, Example 8, below, for details.

FIG. 11 shows X-rays of an ulnar critical size defect in a rabbit treated with a blood coagulum containing BMP-7 (100 µg) at 6 weeks (FIG. 11A) and at 8 weeks (FIG. 11B) as described in Example 9. The X-rays indicate that the coagulum fell apart at an early time point and only spots of mineralized tissue are evident in the defect area.

DESCRIPTION OF THE INVENTION

Figure 1:
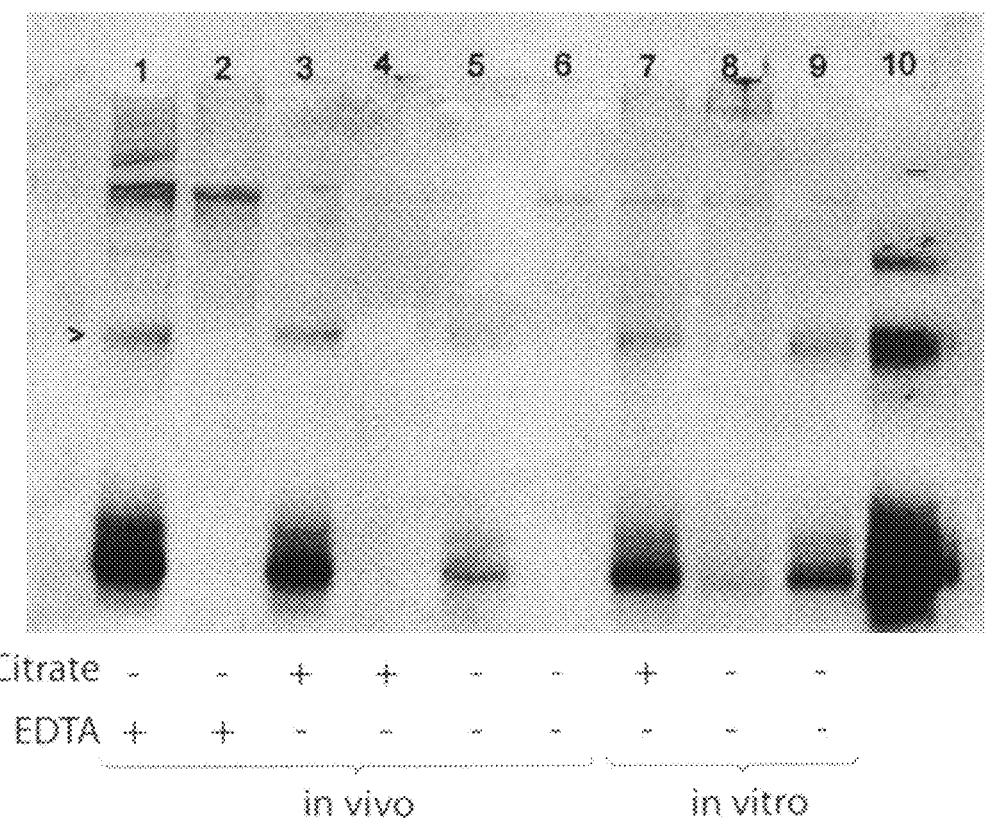
FIG. 1 shows a Western immunoblot of the recovery of soluble BMP-7 (sBMP) from blood samples. Lanes 1-6 show "in vivo" blood samples, i.e., blood samples obtained from rats after injection with sBMP-7. Lanes 7-9 show "in vitro" blood samples, i.e., blood samples obtained from rats and then spiked with sBMP-7. Lane 1: Blood sample from rat injected with sBMP-7 collected into tube with EDTA. Lane 2: Blood sample from control rat collected into tube with EDTA. Lane 3: Blood sample from rat injected with sBMP-7 collected into tube with citrate. Lane 4: Blood sample from control rat collected into tube with citrate. Lane 5: Blood sample from rat injected with sBMP-7 collected into tube without added anticoagulants. Lane 6: Blood sample from control rat collected into tubes without added anticoagulants. Lane 7: Blood sample from rat collected into citrate tube in which 100 ng of BMP-7 was added (spiked) immediately after drawing blood. Lane 8: Blood sample from rat collected into tube without added anticoagulants in which 100 ng of sBMP-7 was added immediately after drawing blood. Lane 9: Blood sample from rat collected into tube without added anticoagulants in which 100 ng of sBMP-7 was added after formation coagulum took place. Lane 10: sBMP-7 standard 200 ng. See, Example 1, below for details.

The invention is based on the discovery that whole blood drawn from an individual can be employed in a composition to provide a useful and affordable carrier for the administration of an osteogenic compound, such as an osteogenic bone morphogenetic protein (BMP), to a bone defect. In particular, the invention provides a whole blood-derived coagulum device (WBCD) that may be prepared for administration to a bone defect in an individual within an hour or less of preparing the device.

In order that the invention may be more clearly understood, the following terms are defined.

The terms "bone morphogenetic protein", "BMP", and "morphogen" are synonymous and refer to any member of a particular subclass (i.e., the BMP family) of the transforming growth factor-β (TGF-β) super family of proteins (see, e.g., Hoffmann et al., *Appl. Microbiol. Biotechnol.*, 57: 294-308 (2001); Reddi, *J. Bone Joint Surg.*, 83-A(Supp. 1): S1-S6 (2001); U.S. Pat. Nos. 4,968,590; 5,011,691; 5,674,844; 6,333,312). All such BMPs have a signal peptide, prodomain, and a carboxy-terminal (mature) domain. The carboxy-terminal domain is the mature form of the BMP monomer and contains a highly conserved region characterized by seven cysteines that form a cysteine knot (see, Griffith et al., *Proc. Natl. Acad. Sci. USA.*, 93: 878-883 (1996)).

BMPs were originally isolated from mammalian bone using protein purification methods (see, e.g., Urist et al., *Proc. Soc. Exp. Biol. Med.*, 173: 194-199 (1983); Urist et al., *Proc. Natl. Acad. Sci. USA,* 81: 371-375 (1984); Sampath et al., *Proc. Natl. Acad. Sci. USA,* 84: 7109-7113 (1987); U.S. Pat. No. 5,496,552). However, BMPs have also been detected in or isolated from other mammalian tissues and organ including kidney, liver, lung, brain, muscle, teeth, and gut. BMPs may also be produced using standard in vitro recombinant DNA technology for expression in prokaryotic or eukaryotic cell cultures (see, e.g., Wang et al., *Proc. Natl. Acad. Sci. USA,* 87: 2220-2224 (1990); Wozney et al., *Science,* 242: 1528-1534 (1988)). Some BMPs are commercially available for local use as well (e.g., BMP-7 is manufactured and distributed for treatment of long bone non-union fractures by Stryker-Biotech (Hopkinton, Mass., U.S.); BMP-2 is manufactured and distributed for long bone acute fractures by Wyeth (Madison, N.J., U.S.), and also for spinal fissions by Medtronic, Inc., Minneapolis, Minn., U.S.).

BMPs normally exist as dimers of the same monomeric polypeptides (homodimers) held together by hydrophobic interactions and at least one interchain (between monomers) disulfide bond. However, BMPs may also form heterodimers by combining the monomers of different degrees (lengths) of processing (e.g., a full-length, unprocessed monomer associated with a processed, mature monomer) or monomers from different BMPs (e.g., a BMP-6 monomer associated with a BMP-7 monomer). A BMP dimer of unprocessed monomers or a BMP heterodimer of one processed BMP monomer and one unprocessed BMP monomer are typically soluble in aqueous solutions, whereas a BMP homodimer comprised of two fully processed (mature) monomers is only soluble in an aqueous solution at a low pH (e.g., acetate buffer, pH 4.5) (see, e.g., Jones et al., *Growth Factors,* 11: 215-225 (1994)).

BMPs useful in the compositions and methods described herein are those that have osteogenic activity, i.e., the ability to stimulate bone formation. Osteogenic (or "osteoinductive") activity may be detected using any of a variety of standard assays. Such osteogenic assays include ectopic bone formation assays in which a carrier matrix comprising collagen and a BMP are implanted at an ectopic site in a rodent, and the implant then monitored for bone formation (Sampath and Reddi, *Proc. Natl. Acad. Sci. USA,* 78: 7599-7603 (1981)). In a variation of such an assay, the matrix may be implanted at an ectopic site and the BMP administered to the site, e.g., by intravenous injection into the rodent. Another way to assay for BMP osteogenic activity is to incubate cultured fibroblast progenitor cells with a BMP and then monitor the cells for differentiation into chondrocytes and/or osteoblasts (see, e.g., Asahina et al., *Exp. Cell. Res.,* 222: 38-47 (1996)). BMPs that have osteogenic activity and that are therefore useful in the compositions and methods described herein include, but are not limited to, BMP-2, BMP-4, BMP-6, BMP-7, BMP-9, BMP-12, BMP-13, and heterodimers thereof, whether purified from a natural source, produced recombinantly by eukaryotic (e.g., mammalian, yeasts, insects, fish) or prokaryotic (e.g., bacterial) cells, or produced in whole or in part by in vitro protein synthesis methods. A BMP that has an osteogenic activity may also possess one or more other beneficial pharmacological activities such as the ability to restore or regenerate damaged soft tissues or organs, e.g., ischemic kidneys (Vukicevic et al., *J. Clin. Invest.* 102: 202-214 (1998)).

It is also understood that compositions and methods as described herein may alternatively comprise an osteogenic protein other than a member of the osteogenic BMP family described above provided such osteogenic protein is functionally equivalent to a BMP in that the protein has osteogenic activity as demonstrated in a standard osteogenic assay, such as an ectopic bone formation assay described above. Functionally equivalent proteins may include various osteogenic BMP homologues, i.e., osteogenic proteins that have an amino acid sequence that is homologous to a known osteogenic BMP (e.g., about 80% or more homologous to a known osteogenic protein). Such BMP homologues may be naturally occurring, recombinantly produced, or synthetically produced in whole or in part (see, e.g., U.S. Pat. Nos. 5,674,844; 6,333,312).

The terms "disorder" and "disease" are synonymous, and refer to any pathological condition irrespective of cause or etiological agent.

By "pharmaceutically acceptable" is meant a material that is not biologically, chemically, or in any other way, incompatible with body chemistry and metabolism and also does not adversely affect the desired, effective activity of an osteogenic BMP or any other component in a composition that may be administered to an individual to treat a bone defect according to the invention. Only pharmaceutically acceptable components are used in preparing a WBCD of the invention for treating bone defects in an individual (human or other mammal).

"Cohesive" as used herein to describe a coagulum gel means that, in the absence of being divided by a force (e.g., the edge of a spatula), the coagulum gel has a self-supporting, adhesive and viscous nature and is not a free flowing liquid or a collection of separated domains or pieces.

"Gel" means a semi-solid jelly-like material.

"Homogeneous" or "homogenous", as applied to a coagulum gel, means that the coagulum gel has a uniform consistency as opposed to a nonuniform fibrous network connecting clumps of clots.

"Syringeable" as used herein to describe a coagulum gel means that the coagulum gel can be drawn up into a syringe with a needle in the range of 18 to 23 gauge, inclusive, without clogging the needle or breaking up into clumps.

"Injectable" as used herein to describe a coagulum gel means that the coagulum gel can be expelled from a syringe through the aperture of the syringe or through a needle in the range of 18 to 23 gauge, inclusive, without clogging the aperture or needle and without breaking up into clumps.

"Malleable" as used herein to describe a coagulum gel means that the coagulum gel is capable of being shaped or formed to fill or cover a bone defect. A malleable coagulum gel is self-supporting (or mechanically stable) and will substantially retain the shape into which it was formed.

Unless stated otherwise, a numerical range, e.g., for amounts, concentrations, time, or distance, includes the numerical values at the lower and higher ends of the range.

The meaning of other terms will be evident by the context of use and, unless otherwise indicated, are consistent with the meanings understood by those skilled in the art, including the fields of tissue regeneration, medicine, pharmacology, metabolic bone disorders, and molecular biology.

As shown herein, osteogenic BMPs disappear from blood undergoing coagulation (clotting) and become localized in the coagulum. In particular, osteogenic BMPs have an affinity for several molecules in serum and in blood coagulum. In addition, as shown herein, the consistency of a blood coagulum can be modified so that it has the proper integrity and other properties required for delivering an effective amount of an osteogenic BMP to a site of a bone defect. Unlike an unmodified blood coagulum, a whole blood-derived coagulum device (WBCD) as described herein is a coagulum gel that is homogenous, cohesive, syringeable, injectable, and malleable. These properties are obtained by adding a sufficient amount of exogenous calcium ion to whole blood and permitting coagulation to occur. Accordingly, a WBCD described herein is readily made, manipulated, and administered to a bone defect. Bone defects that may be treated with a WBCD as described include fractures and bone characterized by inadequate bone growth as occurs in various metabolic bone diseases, including, but not limited to, osteoporosis, osteopenia, and Paget's Disease.

A WBCD of the invention may be conveniently administered to a bone defect of an individual by injection using a syringe optionally equipped with a needle, preferably in the range of 18 to 23 gauge, inclusive, or applied to a bone defect with a spatula during surgery.

In a preferred embodiment, the invention provides a whole blood-derived coagulum device (WBCD) for treating a bone defect in an individual prepared by the steps comprising:
   (a) combining:
      (1) whole blood,
      (2) an osteogenic protein,
      (3) exogenously provided calcium ion, and
      (4) optionally, an exogenously provided fibrin-thrombin mixture,
   (b) incubating the ingredients combined in step (a) until a mechanically stable coagulum is formed,
wherein the exogenously provided calcium ion is present at a concentration that is effective to provide a homogeneous, cohesive, syringeable, injectable, and malleable coagulum gel.

Preferably, the whole blood used in the preparation of a WBCD described herein is autologous whole blood drawn from the individual in need of treatment as autologous whole blood does not introduce any potential immunogens into the individual. Nevertheless, it is recognized that in some situations, crossmatched whole blood may be used as, e.g., when a patient may already have lost a significant amount of blood or may already be receiving a blood transfusion. In such situations, the use of crossmatched whole blood in a WBCD introduces the same or similar risks of serum sickness associated with any transfusion employing crossmatched whole blood.

A WBCD described herein is prepared using exogenously provided calcium ion. The amount of calcium largely controls the properties of the coagulum gel that enable the WBCD to not only be easily manipulated and administered (e.g., by injection or implantation) to a defect site but also to be maintained in the defect site for a sufficient period of time without washing or flowing out to promote growth of new bone to fill the defect or rebridge the bone ends of a defect, including some critical size, non-union fractures. Accordingly, calcium ion is added to whole blood in an amount sufficient to provide a homogeneous, cohesive, syringeable, injectable, and malleable coagulum gel. Such properties of the coagulum gel are also provided if the exogenously provided calcium ion is present in the range of 1 mM to 2.5 mM, inclusive. A preferred source of calcium ion is calcium chloride. A preferred range for using exogenously added calcium chloride in a WBCD described herein is 5 mM to 15 mM, inclusive. When exogenously provided calcium ion is present at a concentration greater than 2.5 mM or when exogenously provided calcium chloride is present at a concentration greater than 15 mM, the coagulum gel is not a homogeneous, cohesive, syringeable, injectable, and malleable gel, but is too rigid and brittle for manipulation and administration into defects.

Preferably, a WBCD is also prepared with an exogenously provided mixture of fibrin and thrombin. Fibrin-thrombin mixtures useful in a WBCD described herein may be made by simply mixing fibrin and thrombin in with the other ingredients of the WBCD. Alternatively, fibrin and thrombin may be premixed or purchased as a mixture and the mixture then added to the other ingredients. Fibrin-thrombin mixtures useful in a WBCD include those known in the art as "fibrin glue" or "fibrin sealant". Commercial preparations of fibrin-thrombin mixtures, fibrin glues, and fibrin sealants are readily available. Fibrin and thrombin used in preparing a WBCD as described herein are of pharmaceutically acceptable quality and are not a source of significant immunogenicity that would normally elicit an immune response in most individuals.

An exogenously provided fibrin-thrombin mixture may enhance one or more of the properties provided to the coagulum gel by calcium ion as mentioned above. In addition, a fibrin-thrombin mixture can also be used to entrap the osteogenic protein component of a WBCD. Such entrapment of the osteogenic protein enhances retention of the osteogenic protein by the WBCD and thereby decreases the rate of migration of the osteogenic protein from the WBCD and the local defect site to which the WBCD has been applied. Enhanced retention of an osteogenic protein in a WBCD is particularly important as the size of a defect increases or the distance between bone ends of a defect increases because in such defects increasingly more new bone needs to grow to fill the defect or rebridge the bone ends of the defect. The longer the period of time that osteogenic protein persists locally in a defect site, the longer the period of time that new bone formation can be stimulated by the osteogenic protein.

Preferably, the exogenously provided fibrin-thrombin mixture used in a WBCD described herein provides fibrin in the range of 5 mg/mL to 10 mg/mL, inclusive, and provides thrombin in the range of 0.5 mg/mL to 5 mg/mL. A fibrin-thrombin mixture is particularly preferred to entrap an osteogenic BMP and thereby enhance retention of the BMP in the WBCD locally in a defect site. The presence of a fibrin-thrombin mixture also enhances the consistency and other features of the WBCD. Accordingly, lower concentrations of the above-mentioned concentration range may be used as the size of a bone defect decreases or as the distance to be rebridged by new bone growth between bone ends of a defect decreases.

Incorporating an exogenously provided fibrin-thrombin mixture into a WBCD is particularly useful to entrap the osteogenic protein ingredient prior to addition of whole blood and its subsequent coagulation. As mentioned above, such entrapment of the osteogenic protein ingredient in a fibrin-thrombin matrix prior to coagulation increases the retention of the osteogenic protein in the WBCD, leading to an enhanced rate of healing of the defect to which the WBCD is administered. Moreover, enhancing retention of the osteogenic protein is particularly beneficial when a WBCD is administered to defect in an area of the body that has little or no local tissue source of endogenous osteogenic proteins, e.g., as may be the case in treating dental or periodontal defects. Accordingly, in view of the benefit of enhancing retention of the osteogenic protein ingredient in a WBCD and thereby enhancing retention of the protein locally at a defect, the incorporation of a fibrin-thrombin mixture into a WBCD is highly recommended and preferred, even if a defect is relatively small or the bone ends of a fracture are very close or contacting one another.

Enhanced entrapment of an osteogenic protein is easily accomplished in preparing the WBCD as mentioned above, except that step (a) is carried out by preparing a first mixture by combining the exogenously provided fibrin-thrombin mixture, the exogenously provided calcium ion, and the osteogenic protein, followed by incubating the first mixture for at least 15 minutes, and thereafter adding the whole blood to the first mixture to form a second mixture, and incubating the second mixture for about 20 minutes. This embodiment entraps the osteogenic BMP in the fibrin-thrombin mixture and thereby enhances retention of the BMP in the WBCD. In this way, the migration of the osteogenic protein out of the area of the local defect site to which the WBCD is applied is decreased, which in turn increases the period of time over which new bone formation is stimulated by the osteogenic protein.

Any of a variety of osteogenic BMPs may be used in the invention. Preferably, an osteogenic BMP used in the compositions and methods described herein is selected from the group consisting of BMP-2, BMP-4, BMP-6, BMP-7, heterodimers thereof, and combinations thereof. Any of a variety of osteogenic proteins may be used in a WBCD described herein. Preferably, the osteogenic protein is an osteogenic bone morphogenetic protein (BMP). More preferably, an osteogenic BMP useful in the compositions and methods described herein is selected from the group consisting of BMP-2, BMP-4, BMP-6, BMP-7, heterodimers thereof, and combinations thereof. Preferably, a BMP or other osteogenic protein is present in a WBCD described herein at a concentration in the range of 50 µg/mL to 500 µg/mL.

A WBCD described herein may be used in combination with any of a variety of rods, screws, and other apparatuses employed by orthopedic surgeons to reconnect and brace bones that have sustained major fractures or loss of bone mass. Such conditions include, but are not limited to, critical size non-union fractures, multiple or compound fractures of one or more bones, and exceptional degeneration of bone mass. A WBCD may be injected or implanted in any defect or on any bone surface as part of such major surgery or reconstruction. A WBCD may also be applied to prosthetics, such as artificial hips and knees, and to pins that are to be inserted permanently into the skeleton of an individual. Owing to its properties, a WBCD described herein may also be used in reconstructive or cosmetic surgery to restore, enhance, or modify features, e.g., in the face and head, for which increased bone mass may be required. This is particularly important in the case of facial and head features that may have been lost or diminished due to loss of bone mass as the result of trauma or disease.

The induction of new bone formation with a WBCD containing an osteogenic BMP showed accelerated bone healing both as compared to current standard care of treatments and to a commercially used bovine collagen based BMP device (see, Example 8, below).

The compositions and methods described herein may also be used in dental and periodontal procedures to regenerate dentin and periodontal tissue, including bone, cementum, and periodontal ligament.

Also provided are kits for preparing a WBCD for treating bone defects in an individual. For example, in a preferred embodiment, a kit for preparing an osteogenic whole blood-derived coagulum (WBCD) device for treating bone defects comprises:

1. a vial containing a lyophilized osteogenic BMP,
2. a buffer for reconstituting the lyophilized BMP powder,
3. a syringe for reconstituting the lyophilized BMP in the buffer,
4. a vaccutaner for collecting a patient's blood,
5. a sterile solution of 1 M $CaCl_2$,
6. a fibrin-thrombin mixture,
7. a container for mixing whole blood with the reconstituted BMP,
8. a spatula and/or a syringe for applying the WBCD to bone ends or bone defects during open surgery, and
9. instructions for the preparation and use of the WBCD using autologous or crossmatched blood.

A WBCD as described herein may be used immediately after being prepared to treat an individual or stored for future use in treating the individual. The WBCD is ready for use as soon as it reaches a desired consistency, in order to be semi-solid and malleable but still syringeable and injectable. Preferably, a WBCD as described herein is used within about 15 to 45 minutes from the beginning of its preparation. This is a particularly convenient time schedule with respect to conducting many, if not most, orthopedic surgical operations.

In order to more fully illustrate the invention, the following non-limiting examples are provided.

EXAMPLES

Example 1

Binding of Spiked Bone Morphogenetic Protein-7 (BMP-7) to Whole Blood

Materials and Methods

The biodistribution of BMP-7 in biological fluids was evaluated using Western immunoblot analysis of serum and plasma from 5 month-old Sprague-Dawley rats taken 5 minutes after intravenous (i.v.) administration of BMP-7 (25 µg/kg soluble BMP-7). Rats were first injected with 25 µg/kg of soluble form of BMP-7 molecule (sBMP-7) into the tail vein, and blood samples were collected 5 minutes later. These samples are referred to as "in vivo" samples. Also evaluated were rat blood samples to which BMP-7 was added (spiked) to blood drawn from rats into tubes. These samples are referred to as "in vitro" samples. Volume of each blood sample was 1 ml.

Blood samples were drawn from rat orbital plexus into standard hematological tubes with and without an anticoagulant substance (citrate and EDTA). Ex vivo BMP-7 (100 ng of BMP-7) was added directly into the tubes with blood samples immediately after taking blood.

Formation of Cross-Linked Complex and Immunoprecipitation

A mouse monoclonal antibody (Genera Research Laboratory) against a monomeric mature domain of BMP-7 molecule was incubated with protein G agarose beads for 15 minutes on a shaker. In order to retrieve the mouse monoclonal antibody (MAb) from rat sera by protein G, the anti-BMP MAb was immobilized on protein G Sepharose before adding them to rat serum samples. In this way, the mouse MAb could be recovered out of a 1000-fold excess of human IgG.

A rabbit polyclonal antibody (Genera Research Laboratory), which recognizes the prodomain and mature form of BMP-7, was then added to the complex and incubated for another 15 minutes. The samples were centrifuged for 2 minutes on 12,000×g, and the excess of serum was removed. Formulin (500 µl of 4% formalin) was then added to the pellet and incubated for another 30 minutes on a shaker. The sample was centrifuged for 2 minutes on 12,000×g, and the supernatant was removed. The complex was resuspended in a phosphate-buffered saline (PBS) and added into collected serum or plasma samples for immunoprecipitation.

Samples of unclotted blood and sera from clotted blood were incubated with antibody-coupled beads overnight. After that, the samples were centrifuged for 2 minutes on 12,000×g. Supernatant was removed, and the pellets were washed three times with phosphate-buffered saline, and prepared for a gel electrophoresis.

Gel Electrophoresis and Western Immunobloting

The aliquots of the samples were analyzed by electrophoresis and immunoblotting in a Novex mini-gel system. Sodium dodecyl sulfate (SDS) polyacrylamide gel electrophoresis sample buffer was added to the pellet. The samples were denatured by heating at 99° C. for 3 minutes. After that, the samples were centrifuged for 2 minutes on 12,000×g. Supernatants were analyzed on a 10% polyacrylamide/SDS gel (Invitrogen). Proteins were transferred by electro blotting to a nitrocellulose membrane and incubated first with the mouse MAb and rabbit polyclonal BMP-7 antibody. The bound antibodies were detected with alkaline phosphatase-conjugated anti-mouse and anti-rabbit IgG immunoglobulin (Immunodetection Kit, Invitrogen).

Results

A large amount of BMP-7 added to whole blood remains in the subsequently formed coagulum (blood clot). This was confirmed by analyzing serum samples by immunoprecipitation with cross-linked antibodies (FIG. 1). Blood samples from a rat injected with BMP-7 collected into tubes with EDTA as anticoagulant (FIG. 1, lane 1) showed a better recovery of BMP-7 than samples collected into tubes containing citrate as anticoagulant (FIG. 1, lane 3) or tubes without anticoagulants (FIG. 1, lane 5). The same result was obtained when blood samples were spiked with BMP-7 immediately after drawing the blood from orbital plexus into the tubes (FIG. 1, lane 7). Recovery of added BMP-7 into the blood from tubes without anticoagulants was very low (FIG. 1, lane 5 and 8). Also, a relatively good recovery was obtained when BMP-7 was added to samples after the coagulum was already formed (FIG. 1, lane 9). Using EDTA and citrate to prevent blood coagulation confirmed that recovery of BMP-7 was better than in samples without blood anticoagulants. This was due to binding of BMP-7 to blood components like fibrin, fibrinogen, alpha-1-globulin, alpha-2-globulin, alpha 2-macroglobulin, beta-2-microglobulin and platelets as demonstrated by dot blots where the aforementioned blood components were dotted on nitrocellulose paper to which BMP-7 was added. These results lead to the conclusion that BMP-7 added to whole blood is not detected in the supernatant following formation of a blood clot (coagulum) due to binding to various blood component molecules. BMP-7 remained in the coagulum and could not be recovered after the coagulum was formed (FIG. 1, lane 8).

Conclusion

A large amount of BMP-7 added to whole blood is retained in the subsequently formed coagulum as confirmed by analyzing serum samples by immunoprecipitation with cross-linked antibodies. BMP-7 added to whole blood is not detected in the supernatant following formation of blood clot due to binding to various blood component molecules. BMP-7 remained in the coagulum and could not be recovered in the supernatant serum after the coagulum was formed. This surprising discovery is the basis for developing a whole blood-derived coagulum device (WBCD) as described herein for treating bone defects.

Example 2

Binding of 99 mTc Labeled BMP-6 to Whole Blood Samples

Materials and Methods

Sprague-Dawley rats 4-6 months old were used. Blood samples (1 ml) were collected from the venous orbital plexus into tubes without adding anticoagulant.

BMP-6 Labeling

Mature BMP-6 was chelated with mercaptoacetylthreeglycin (MAG3), and then the complex was labeled with radioactive 99m Technetium-pertechnetate (99mTc). Chromatography revealed that more than 97% of 99 mTc was ligated to the complex.

Protocol

Different amounts of labeled BMP-6 were added to the whole blood samples. In 1 ml of whole rat blood was added 2, 5, or 10 µg of labeled protein (concentration of labeled BMP-6 was 1 µg/ml). After coagulum formation, the samples were centrifuged 10 minutes at 8000×g to separate serum from the clot. The amount of radioactivity was measured separately in the whole blood, serum, and clot with a gamma counter.

Measurement of Radioactive BMP-6

Amount of radioactivity was measured with a gamma counter and was expressed as counts per minute (cpm). The results were expressed as a percentage of the applied doses, comparing the measured radioactivity with radioactivity of a standard that had the same radioactivity as the total spiked dose. All values were corrected in dependence for the half-life factor of 99 mTc.

Results

Figure 2:
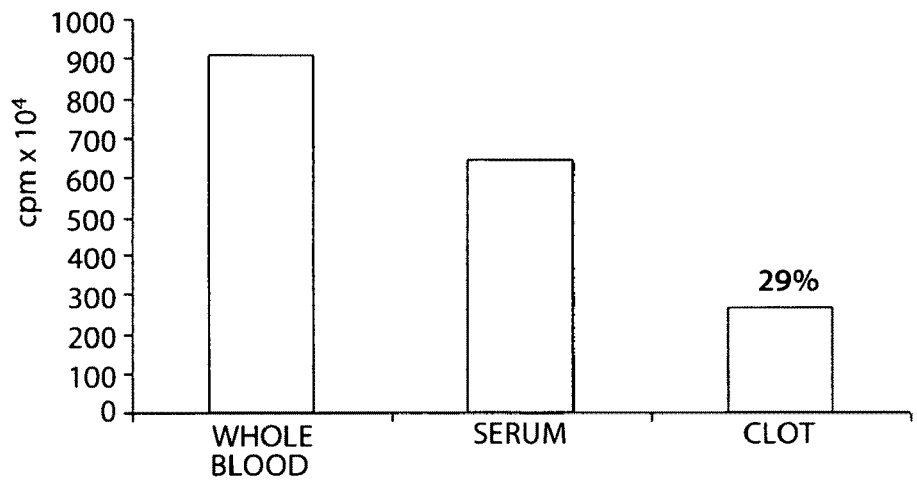
FIG. 2 shows the retention of 2 μg (9,147,376 cpm) of BMP-6 MAG3-99 mTc protein added to 1 ml samples of whole rat blood. The amount (in cpm) of the labeled BMP-6 retained in the serum fraction and in the clot of the whole blood is also shown. 29% (266,0594 cpm) of the labeled BMP-6 was retained in the clot. See, Example 2, below, for details.
Figure 3:
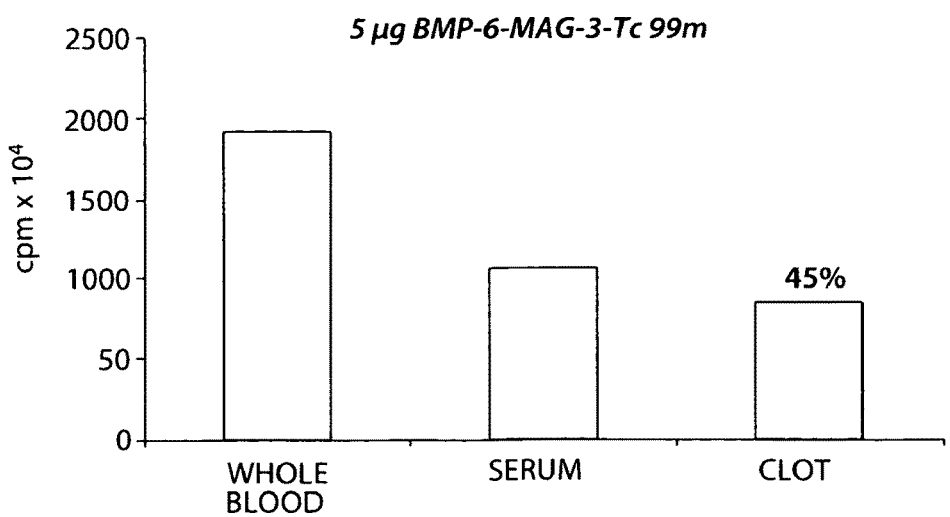
FIG. 3 shows the retention of 5 μg (1,924,768 cpm) of BMP-6 MAG3-99 mTc added to 1 ml samples of whole rat blood. The amount (in cpm) of the labeled BMP-6 retained in the serum fraction and in the clot of the whole blood is also shown. 45% (8,586,759) of the labeled BMP-6 protein was retained in the clot. See, Example 2, below, for details.
Figure 4:
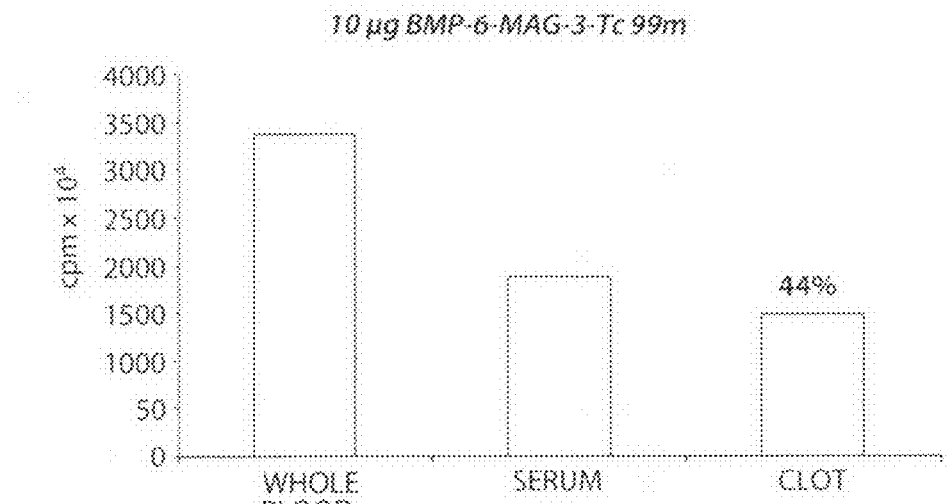
FIG. 4 shows the retention of 10 μg of BMP-6 MAG3-99 mTc (33,690,011 cpm) added to 1 ml samples of whole rat blood. The amount (in cpm) of the labeled BMP-6 retained in the serum fraction and in the clot of the whole blood is also shown. 44% (14,824,426 cpm) of the labeled BMP-6 protein was retained in the clot. See, Example 2, below, for details.

Addition of 2 µg (9,147,376 cpm) of BMP-6 labeled protein to 1 ml whole rat blood samples resulted in retention of 29% (266,0594 cpm) of the labeled BMP-6 in the clot (FIG. 2). Addition of 5 µg of 99 mTc BMP-6 (1,924,768 cpm) to 1 ml samples of whole rat blood resulted in retention of 45% (8,586,759) of labeled BMP-6 in the clot, and addition of 10 µg of 99 mTc BMP-6 (33,690,011 cpm) to 1 ml samples of whole rat blood resulted in retention of 44% (14,824,426 cpm) of labeled BMP-6 protein in the clot (FIGS. 3 and 4).

Conclusion

A maximal retention of increasing doses of 99 mTc BMP-6 added to whole blood was 45% in the blood clot. This may reflect the specific differences of binding of 99 mTc labeled proteins or a difference between BMP-6 and BMP-7 biology. MAG3 may also influence binding capability of BMP-6 to blood components.

Example 3

Biological Availability of BMP-7 in Rat Circulation

Materials and Methods

"In vivo" sera or plasma samples were rat blood samples analyzed after systemic administration to rats of soluble BMP-7 (25 µg/kg). "In vitro" samples were samples in which sBMP-7 (100 ng) was added to blood samples immediately after being drawn from rats as well as 5 minutes later. Blood samples were collected from venous orbital plexus into tubes with and without anticoagulant substance (citrate and EDTA).

Antibodies Immobilized and Chemically Cross-Linked to Protein G Agarose

IgG from serum produced heavy bands on the gel and subsequently reacted with the second antibody. In order to prevent the IgG from entering the gel, we cross-linked the mouse monoclonal BMP-7 antibody to protein G Sepharose using 4% formaldehyde solution. The recovery in immunoprecipitates was almost complete even after cross-linking for 30 minutes with formalin.

Formation of Cross-Linked Complex and Immunoprecipitation

A mouse monoclonal antibody (Genera Research laboratory) against a monomeric mature domain of BMP-7 molecule was incubated with protein G agarose beads for 15 minutes on a shaker as described above in Example 1.

Gel Electrophoresis and Western Immunoblot

The aliquots of the samples were analyzed by electrophoresis and immunoblotting in a Novex mini-gel system as described in Example 1.

Protocol

The rats were injected with BMP-7 (250 µg/kg). Blood samples were collected into tubes with EDTA at 1, 5, 10, 15, 20, and 30 minutes after injection. In vitro recovery of exogenously added BMP-7 from rat serum was tested in whole blood samples collected into tubes without added anticoagulants.

Results

Figure 5:
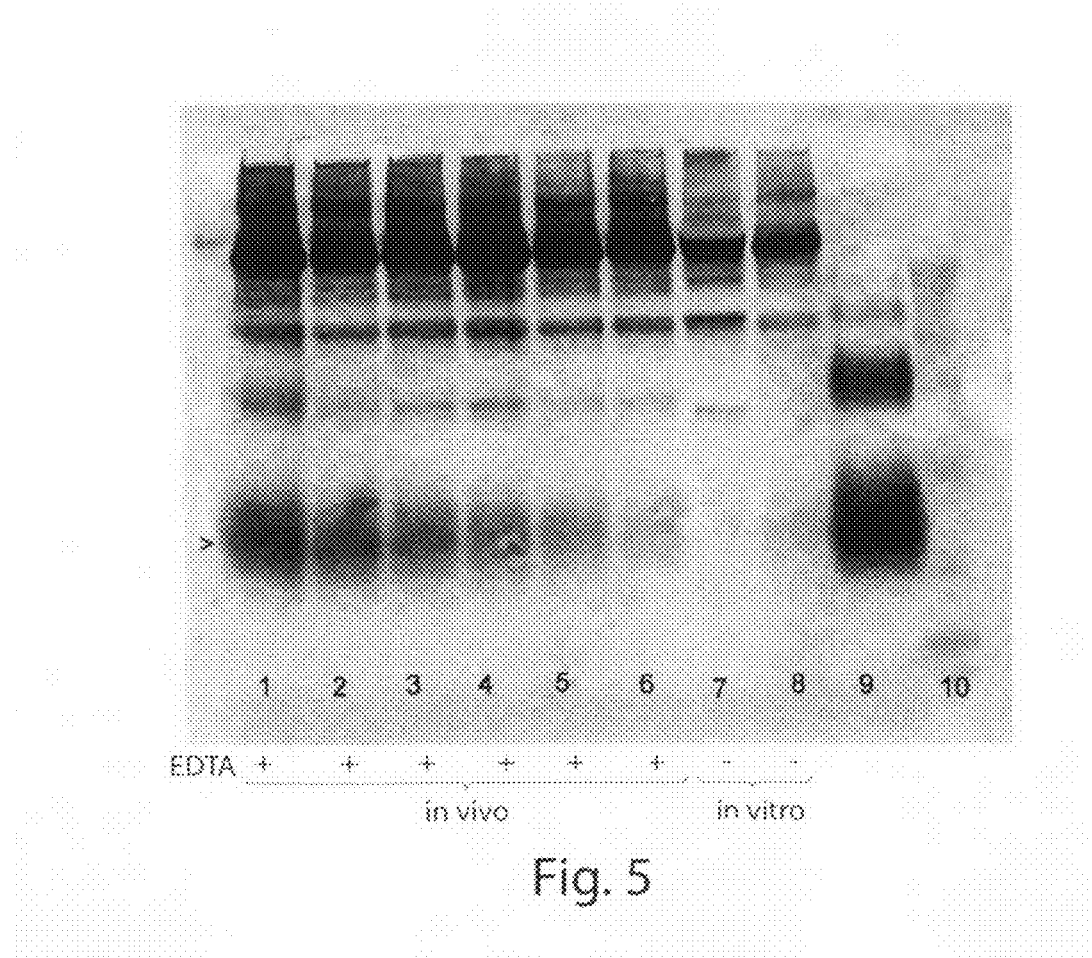
FIG. 5 shows a Western immunoblot of BMP in various blood samples. Lanes 1-6 show "in vivo" blood samples, i.e., blood samples obtained from rats after injection with sBMP-7. Lanes 7 and 8 show "in vitro" blood samples, i.e., blood samples obtained from rats and then spiked with sBMP-7. Lane 1: Blood sample 1 minute after injection of rat with sBMP-7 collected into tube containing EDTA. Lane 2: Blood sample 5 minutes after injection of rat with sBMP-7 collected into tube containing EDTA. Lane 3: Blood sample 10 minutes after injection of rat with sBMP-7 collected into tube containing EDTA. Lane 4: Blood sample 15 minutes after injection of rat with sBMP-7 collected into tube containing EDTA. Lane 5: Blood sample 20 minutes after injection of rat with sBMP-7 collected into tube containing EDTA. Lane 6: Blood sample 30 minutes after injection of rat with sBMP-7 collected into tube containing EDTA. Lane 7: Blood sample from a rat collected into tube without added anticoagulants in which 100 ng of sBMP-7 was added immediately after being drawn ("in vitro"). Lane 8: Blood sample from a rat collected into a tube without added anticoagulants in which 100 ng of sBMP-7 was added 5 minutes after drawing the blood. Lane 9: sBMP-7 standard of 200 ng. Lane 10: Standard markers. See, Example 3, below for details.

The results show that BMP-7 was available in serum up to 30 minutes following injection into the rat tail vein (see, "in vivo" samples of FIG. 5, lanes 1-6). In such blood samples collected into tubes containing EDTA and precipitated with cross-linked antibodies, recovery of exogenous BMP-7 was successful. However, recovery of BMP-7 from blood sample to which BMP-7 was added in tubes not containing anticoagulants was unsuccessful (see, FIG. 5, lane 7). Recovery of BMP-7 added to blood 5 minutes after drawing the blood into tubes without anticoagulants (coagulation cascade almost finished) was low (FIG. 5, lane 8).

Conclusion

BMP-7 was available in serum 30 minutes following injection into the rat tail vein after collection of blood into the tubes with EDTA. When the coagulation cascade was prevented with anticoagulant, the BMP-7 could be recovered in the plasma. Immunoprecipitation with the cross-linked antibodies proved to be a highly effective method for analyzing the blood samples.

Example 4

Formulation of a Whole Blood-Derived Coagulum Device (WBCD) as a Carrier of Mammalian Osteogenic BMP Proteins and its Efficacy in a Rat Model of Ectopic Bone Formation Unmodified WBCD Composition (BMP Present, No Calcium Chloride, No Thrombin Reagent)

Blood samples were collected from rat orbital plexus into tubes without any anticoagulant in a volume of 300 µl. Mammalian cell-produced human BMP-2 ("mBMP-2") or *Escherichia coli*-produced human BMP-2 ("*E. coli* BMP-2") was added into the blood in an amount of 25 µg, 50 µg, 100 µg, 200 µg, and 500 µg. Each WBCD composition (see, below) was then left for 2 hours at +4° C. to coagulate. The compositions were centrifuged at 8000×g for 5 minutes, the liquid portion was removed and saved, and the WBCD compositions were ready for use.

WBCD Composition (Modification 1)

Blood samples were collected from rat orbital plexus into tubes without any anticoagulant in a volume of 300 µl. Calcium chloride (100 µl of 1 M CaCl$_2$) was then added into the whole blood. The mammalian BMP-2 or the *E. coli* BMP-2 was added into the blood in an amount of 25 µg, 50 µg, 100 µg, 200 µg, and 500 µg. The WBCD compositions were then left for 2 hours on +4° C. to coagulate. The WBCD compositions were centrifuged and the liquid portion removed as described.
WBCD Device (Modification 2)

Blood samples were collected from rat orbital plexus into tubes without any anticoagulant in a volume of 300 µl. A thrombin reagent (100 µl) prepared with 1 M $CaCl_2$ was added to the whole blood. The mammalian BMP-2 or E. coli BMP-2 was then added in amounts of 25 µg, 50 µg, 100 µg, 200 µg, and 500 µg. The compositions were then left for 2 hours on +4° C. to coagulate. The WBCD compositions were centrifuged and the liquid portion removed as described.
WBCD Device (Modification 3)

Blood samples were collected from rat orbital plexus into tubes without any anticoagulant in a volume of 300 µl. Fibrin sealant (100 µl) was added to the whole blood. Fibrin sealant contains clottable protein, fibrinogen, plasma fibronectin, factor XIII, plasminogen, aprotinin, and thrombin. Calcium chloride (100 µl of 1M $CaCl_2$) was added. Mammalian BMP-2 or E. coli BMP-2 was then added into the blood in amounts of 25 µg, 50 µg, 100 µg, 200 µg, and 500 µg. The composition was then left for 2 hours on +4° C. to coagulate. The WBCD compositions were centrifuged and the liquid portion removed as described above.
WBCD Device (Modification 4—Trapping)

Mammalian BMP-2 or E. coli BMP-2 was added into tubes in amounts of 25 µg, 50 µg, 100 µg, 200 µg, and 500 µg. Fibrin sealant mixture (100 µl) was then added to each tube containing mammalian or E. coli BMP-2 and mixed. The fibrin sealant mixture contained: clottable protein, fibrinogen, plasma fibronectin, factor XIII, plasminogen, aprotinin, thrombin, and 1 M $CaCl_2$. This procedure entraps the BMP in the polymerizing fibrin matrix.

Blood samples were collected from the rat orbital plexus into tubes in a volume of 300 µl and transferred slowly into the polymerizing fibrin matrix containing BMP-2. The WBCD composition device was then left for 2 hours on the room temperature to coagulate. Samples were centrifuged on 8000×g for 5 minutes, the liquid part was removed and saved, and the modified WBCD device was used.
Animals and Treatment Protocol Sprague-Dawley rats, weighing approximately 200 g were subjected to surgery. The WBCD device containing mammalian or E. coli-derived BMP-2 protein was implanted subcutaneously into the axilar region. Animals were divided into the following groups, with four implants per group:
 1. Control animals; implanted WBCD without the osteoinductive protein
 2. WBCD device containing 25, 50, 100, 200, or 500 g of mammalian BMP-2 or E. coli BMP-2 with modifications as indicated above
 3. Helistat (commercial collagen) device containing 25, 50, 100, 200, or 500 µg of mammalian BMP-2 or E. coli BMP-2.

Animals were killed 15 days after surgery, and the implants were fixed and processed for histology and histomorphometry.
Histology Bone pellets were fixed in 4% formalin, decalcified, and embedded in paraffin. Sections were stained with Toluidine blue, Saframin O, alkaline phosphatase (AP), and tartarate resistant acid phosphatase (TRAP). Pellets were considered positive in the presence of new bone formation.
Results The various modified WBCD compositions described above provided similar amounts of newly formed bone. Surprisingly, both mammalian and E. coli-derived BMP-2 containing WBCDs showed similar results in the amount and appearance of bone formed, which is not the case when E. coli BMP-2 is used with Helistat as a carrier. In rats with implanted WBCD devices, there was no inflammatory reaction detectable as compared to the Helistat implant containing E. coli BMP-2 in which there was a pronounced inflammatory response. The distribution of newly formed bone was the best in the WBCD prepared in a process in which the BMP was first trapped in a fibrin matrix (Modification 4, above). In these implants, the distribution of new bone was equal in the middle and at the periphery of the implants. These results indicate that the modified WBCDs provide faster bone formation than a collagen-based device. In addition, WBCDs with trapped BMP showed new bone formation at all implant surfaces within a period of 15 days while a Helistat (collagen) containing device showed a delayed bone formation in the middle of the implant due to decreased penetration of newly formed blood vessels. Finally, both mammalian and E. coli BMP-2 were equally bone inductive when used with the WBCDs. Control animals did not form new bone.

Example 5

Effect of Mammalian BMP-2 and BMP-2 from E. coli on Bone Formation in a Model of Ectopic Bone Formation Demineralized and extracted bone matrix (DBM) was implanted subcutaneously as a surrogate marker of bone formation.
Bone Pellet Donors for bone pellet preparation were Sprague-Dawley rats 20 weeks old. After sacrifice, diaphyses of femurs and tibiae were removed, demineralized, and non-collagenous proteins were extracted with 8 M urea. Subcutaneously implanted pellets of DBM do not induce new bone.
Animals and Treatment Protocol Sprague-Dawley rats, weighing approximately 200 g were subjected to surgery. DBM bone pellets were implanted subcutaneously into the axilar region. Animals were divided into the following groups, with 4 pellets per group:
 1. Control animals. Implanted bone pellets consisted of DBM without addition of an osteoinductive molecule.
 2. Bone pellets with 50 µg of mammalian BMP-2.
 3. Bone pellets with 100 µg of mammalian BMP-2.
 4. Bone pellets with 200 µg of mammalian BMP-2.
 5. Bone pellets with 50 µg of BMP-2 molecule from E. coli.
 6. Bone pellets with 100 µg of BMP-2 molecule from E. coli.
 7. Bone pellets with 200 µg of BMP-2 molecule from E. coli.

Animals were killed 15 days after surgery and bone pellets were taken for histology.
Histology Bone pellets were fixed in 4% formalin, decalcified, and embedded in paraffin. Sections were stained with Toluidine blue, Saframin O, alkaline phosphatase (AP), and tartarate resistant acid phosphatase (TRAP). Pellets were considered positive if new bone formation was observed.
Results Mammalian BMP-2 (mBMP-2) showed better osteoinductive activity in the rat model of ectopic bone formation as compared to BMP-2 from E. coli (E. coli BMP-2) using the same dose and collagen from DBM as a carrier. In DBM bone pellets, which did not contain a BMP, bone formation was not observed.

Bone pellets containing mBMP-2 had more newly formed bone in the middle of implanted DBM bone pellets as compared to BMP-2 from *E. coli*, which was related to increased ingrowth of new blood vessels into the pellets treated with mBMP-2. Newly formed bone expressed as pellet area was increased in mBMP-2 containing 100 and 200 µg as compared to pellets containing similar amounts of *E. coli* BMP-2 (Table 1). Histology sections indicate that both mBMP-2 and *E. coli* BMP-2 were effective in forming new bone at an ectopic site. However, sections of pellets containing *E. coli* BMP-2 showed more inflammatory reaction with a robust pellet capsule formation and lack of newly formed bone in the middle of the pellet. Recombinant human bone morphogenetic proteins, including BMP-2 produced in *E. coli*, may eventually be used in humans, but mammalian BMPs might be more efficacious and less immunogenic when used with heterologous rat collagen carrier (DBM).

TABLE 1

Summarized results of bone formation using mBMP-2 versus *E. coli* BMP-2

| Group | positive/implanted pellet | newly formed bone/pellet area (%) |
| --- | --- | --- |
| Control | 0/4 | 0 |
| mBMP-2 50 µg | 4/4 | 27 |
| mBMP-2 100 µg | 3/4 | 76† |
| mBMP-2 200 µg | 4/4 | 87† |
| *E. coli* BMP-2 50 µg | 2/4 | 24 |
| *E. coli* BMP-2 100 µg | 3/4 | 37 |
| *E. coli* BMP-2 200 µg | 3/4 | 54 |

†significantly different from BMP-2 *E. coli* treated pellets

Example 6

Effect of Mammalian BMP-2 and BMP-7 from Commercial Device on Bone Formation in a Model of Ectopic Bone Formation Demineralized and extracted bone matrix was implanted subcutaneously as a surrogate marker of bone formation.
Bone Pellet
Donors for bone pellet preparation were Sprague-Dawley rats 20 weeks old. After sacrifice diaphyses of femurs and tibiae were removed, demineralized and non-collagenous proteins were extracted with 8 M urea. Subcutaneously implanted pellets of DBM do not induce new bone.
Animals and Treatment Protocol
Sprague-Dawley rats, weighing approximately 200 g were subjected to surgery. DBM bone pellets were implanted subcutaneously into the axilar region. Animals were divided into the following groups, with 4 pellets per group:
1. Control animals. Implanted bone pellets without osteoinductive molecule.
2. Bone pellets with 50 µg of mammalian BMP-2.
3. Bone pellets with 100 µg of mammalian BMP-2.
4. Bone pellets with 200 µg of mammalian BMP-2.
5. Bone pellets with 50 µg of mammalian BMP-7 used for the BMP-7 commercial device.
6. Bone pellets with 100 µg of mammalian BMP-7 used for the BMP-7 commercial device.
7. Bone pellets with 200 µg of mammalian BMP-7 used for the BMP-7 commercial device.
Animals were killed 15 days after surgery and bone pellets were taken for histology.

Histology
Bone pellets were fixed in 4% formalin, decalcified, and embedded in paraffin. Sections were stained with Toluidine blue, Saframin O, alkaline phosphatase (AP), and tartarate resistant acid phosphatase (TRAP). Pellets were considered positive if new bone formation was observed.
Results
Results are shown in Table 2. A similar amount of mammalian BMP-2 showed similar osteoinductive activity in the rat model of ectopic bone formation like mammalian BMP-7 used in the commercial device. In bone pellets of control animals there was no sign of new bone formation.

TABLE 2

| Group | positive/implanted pellet |
| --- | --- |
| Control | 0/4 |
| mBMP-2 50 µg. | 4/4 |
| mBMP-2 100 µg. | 4/4 |
| mBMP-2 200 µg. | 4/4 |
| BMP-7 50 µg | 4/4 |
| BMP-7 100 µg | 4/4 |
| BMP-7 200 µg | 4/4 |

Histological analysis of ectopic bone pellets containing mammalian BMP-2 and mammalian BMP-7 (OP-1) using DBM rat collagen as a carrier showed that the amount and appearance of the newly formed bone were similar with both treatments. This indicates that both mammalian BMPs are equally potent in the bioassay of new bone formation and could therefore be used in bone regeneration with potentially similar treatment outcome.

Example 7

Saturation of WBCD with Different Amounts of BMP-7 Protein

Blood Coagulum Preparation
Blood samples were collected from rat orbital plexus into tubes without any anticoagulant only in control tube, in a volume of 300 µl. Mammalian BMP-7 was added into blood in amounts of 4, 8, 16, and 24 µg. Blood samples were left for 2 hours on +4° C. to coagulate. Samples were centrifuged on 8000×g for 5 minutes, the liquid part was removed and further processed for immunoprecipitation analysis.
Formation of Cross-Linked Complex and Immunoprecipitation
A mouse monoclonal antibody (Genera Research Laboratory) against a monomeric mature domain of BMP-7 molecule was incubated with protein G agarose beads for 15 minutes on a shaker. In order to retrieve the mouse monoclonal antibody (MAb) from rat sera by protein G, the anti-BMP MAb was first immobilized to protein G Sepharose before adding them to rat serum samples. In this way, it was possible to recover the mouse MAb out of a 1000-fold excess of human IgG. After that, a rabbit polyclonal antibody (Genera Research Laboratory), which recognizes prodomain and mature form of BMP-7, was added to the complex and incubated for another 15 minutes. The samples were centrifuged for 2 minutes at 12,000×g, and the excess of serum was removed. Formalin (500 µl of 4% formalin) was then added to the pellet and incubated for another 30 minutes on a shaker. The sample was centrifuged for 2 minutes on 12,000×g, and the supernatant was removed. The complex was resuspended in a phosphate-buffered saline (PBS) and added into collected serum or plasma samples for immunoprecipitation. The samples were incubated with antibody-coupled beads overnight. After that, the samples were centrifuged for 2 minutes on 12,000×g. Supernatant was removed, and the pellets were washed three times with phosphate-buffered saline, and prepared for a gel electrophoresis.

Gel Electrophoresis and Western Immunoblotting

The aliquots of the samples were analyzed by electrophoresis and immunoblotting in a Novex mini-gel system as described in Example 1.

Results

The results indicated that a large amount of BMP-7 added to the blood remained subsequently in the coagulum as confirmed by analyzing serum samples by immunoprecipitation with cross-linked antibodies. Recovery of added BMP-7 in the blood from tubes without anticoagulants was very low.

Example 8

Efficacy of WBCD Containing Recombinant Human BMP-7 in the Healing of a Critical Size Defect of Long Bones in Rabbits Materials and Methods An ulnar segmental-defect model was used to evaluate bone healing in adult male New Zealand White rabbits (2 to 4 kg weight). The implants consisted of blood coagulum as a carrier to which different amounts of recombinant human mature BMP-7 were added (Genera Research Laboratory). These animals were compared with animals receiving blood coagulum alone (negative control) and collagen sponge (HELISTAT®, Integra LifeSciences, Holdings Corp., Plainsboro, N.J.) to which the same amounts of BMP-7 were added (positive control). Rabbits were treated with antiparasitics one week before surgery. Animals are also given enrofloxacin, by intramuscular injection, a day before operation and then ten days following surgery. With the rabbit under anesthesia and analgesia, one forelimb was shaved and then prepared and draped in a sterile fashion. A lateral incision, approximately 2.5 centimeters in length, was made, and the tissues overlying the ulna were dissected. A 1.5-centimeter segmental osteoperiostal defect was created in the middle of the ulna with an oscillating saw. The radius was left intact for mechanical stability, and no internal or external fixation devices were used. After copious irrigation with saline solution to remove bone debris and spilled marrow cells, the implant of the osteogenic protein and the blood coagulum or collagen sponge was packed carefully into place to fill the defect. Coagulum was then overlaid with serum. The soft tissues were closed meticulously in layers to contain the implant. The animals were allowed full weight-bearing activity, water, and rabbit chow.

WBCD Preparation

Blood samples were collected from rabbit marginal ear veins into tubes without any anticoagulants substance in a volume of 1.5 ml, one day before surgery. BMP-7 was added into blood in amounts of 50, 100, and 200 µg. Blood samples were left on +4° C. to coagulate. The next day, samples were centrifuged on 8000×g for 5 minutes. The liquid portion (serum) was removed and saved, and the coagulum was ready to use. Commercial collagen sponges (HELISTAT®) used as positive controls, were soaked with 200 µg of BMP-7, which was added 2 hours prior to implantation (commercial BMP-7 bone device). Rabbits were divided into seven groups of as follows:

Group A: Control. Ulnar critical size defect filled with autologous blood coagulum without BMP-7 (n=8)

Group B: Ulnar critical size defect filled with autologous blood coagulum with 50 µg of BMP-7 (n=8)

Group C: Ulnar critical size defect filled with autologous blood coagulum with 100 µg of BMP-7 (n=8)

Group D: Ulnar critical size defect filled with autologous blood coagulum with 200 µg of BMP-7 (n=8)

Group E: Positive control. Ulnar critical size defect filled with commercial collagen sponges (HELISTAT®, 4.0×3 cm) to which 200 µg of BMP-7 was added (n=8) (commercial BMP-7 bone device)

Group F: Ulnar critical size defect filled with autologous blood coagulum with 50 µg BMP-4 (n=4)

Group G: Ulnar critical size defect filled with autologous blood coagulum with 50 µg BMP-6 (n=2).

Results

Figure 6A:
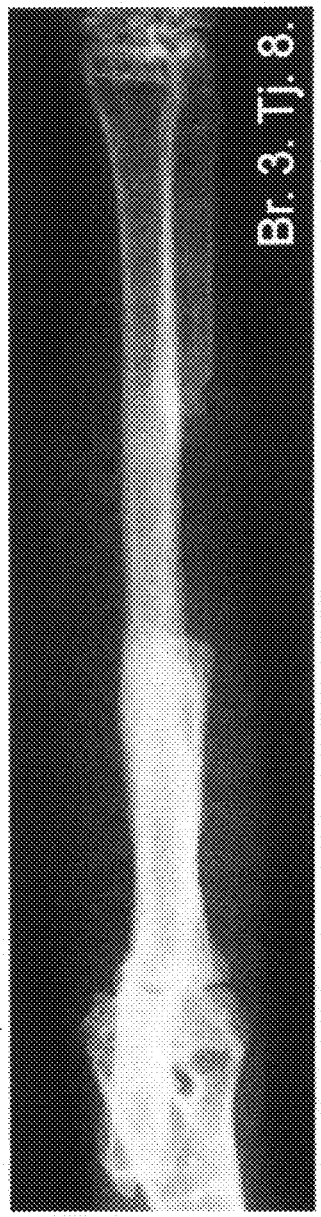
FIGS. 6A and 6B show X-rays of a representative ulnar critical size defect in a rabbit treated with an autologous blood coagulum without BMP-7 ("control WBCD") after 8 weeks (Group A in Example 8). See, Example 8, below, for details.
Figure 6B:
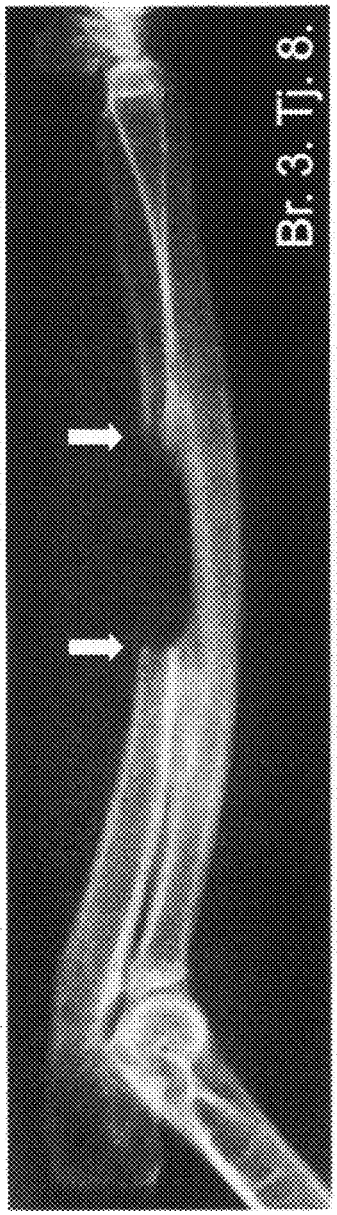

Implants with WBCD containing BMP-7 showed induced complete radiographic osseous union across the defect. None of the control animals treated with WBCD only (i.e., no BMP) achieved full rebridgement of the defect (see, FIGS. 6A and 6B). The BMP-7 implants seem to be similarly active at all given doses.

Group A (Control WBCD, no BMP). None of animals rebridged the defect within of the follow-up period. Callus formed at the free bone ends, but failed to fully rebridge the defect as indicated by X-ray at 8 weeks (see, FIGS. 6A and 6B).

Group B (50 µg of BMP-7 in WBCD). Six out of 8 animals rebridged the defect within the time period of 10 weeks. One animal did not show signs of being healthy.

Group C (100 µg of BMP-7 in WBCD). Seven out of 8 animals rebridged the defect within the time period of 10 weeks. One animal died after operation due of anesthesia. A rebridgement of defect at 8 weeks as indicated by X-ray is shown in FIGS. 7A and 7B.

Group D (200 µg of BMP-7 in WBCD). Eight out of 8 animals rebridged the defect within the time period of 10 weeks.

Group E (commercial collagen sponge to which 200 µg of BMP-7 was added). Eight (n=8) rebridged the defect within the time period of 10 weeks. New bone formation in defect at 8 weeks as indicated by X-ray is shown in FIGS. 8A and 8B.

Example 9

"Normal" (Unmodified) Coagulum Versus WBCD with Calcium and Fibrin Sealant

Blood samples were collected from rabbit marginal ear veins into tubes without any anticoagulants substance in a volume of 1.5 ml, one day before surgery. BMP-7 was added into blood in an amount of 100 µg. Blood samples were left on +4° C. to coagulate. Some blood samples were used as "normal coagulum", i.e., no added calcium chloride or fibrin-thrombin mixture. Other blood samples were used to prepare WBCDs containing added calcium chloride or containing added calcium chloride and added fibrin sealant (fibrin-thrombin mixture). The next day, samples were centrifuged and were implanted into ulnar critical size defects of 8 rabbits.

Results

Figure 9:
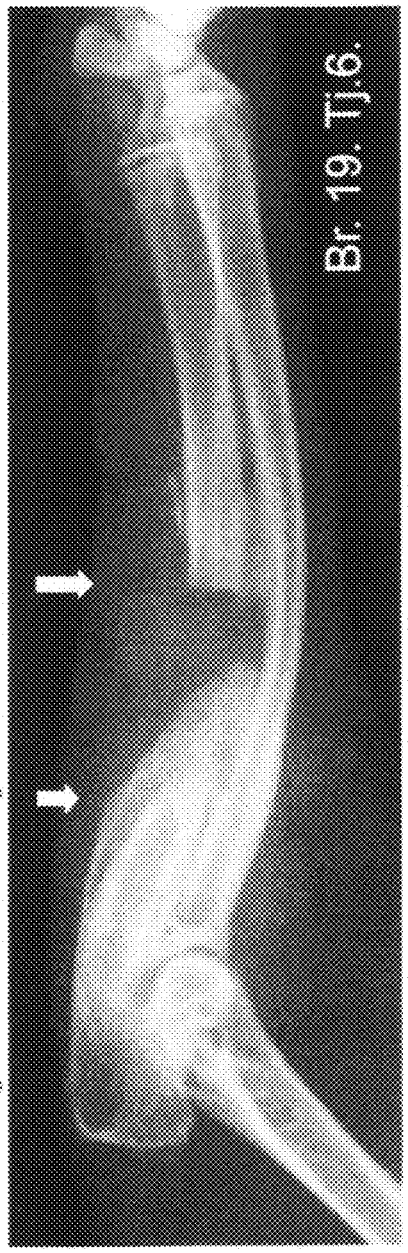
FIG. 9 shows an X-ray of an ulnar critical size defect in a rabbit treated with a blood coagulum containing BMP-7 (100 µg) after 6 weeks as described in Example 9. The X-ray indicates that the consistency of the coagulum was insufficient to maintain a connection between the two bone ends for the period of time needed to form bone throughout the length of the defect.
Figure 10:
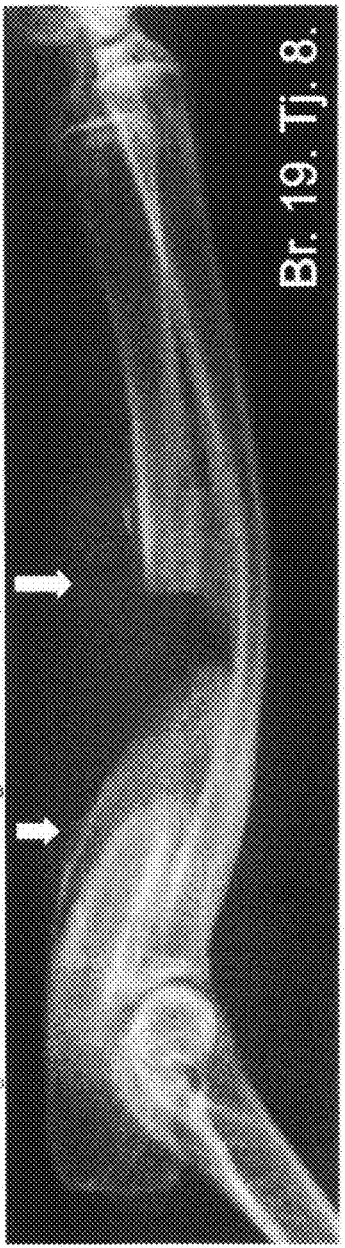
FIG. 10 shows an X-ray of an ulnar critical size defect in a rabbit treated with a blood coagulum containing BMP-7 (100 µg) after 6 weeks as described in Example 9. The X-ray indicates that the consistency of the coagulum was insufficient to maintain a connection between the two bone ends for the period of time needed to form bone throughout the length of the defect.
Figure 12A:
FIG. 12 shows X-rays of an ulnar critical size defect in rabbit treated with a blood coagulum containing exogenously provided calcium chloride (FIG. 12A) or containing exogenously provided calcium chloride and exogenously provided fibrin sealant (fibrin-thrombin mixture) (FIG. 12B) at 8 weeks. Calcium chloride improved the viscosity of the coagulum at the defect site to promote bone growth in the defect as shown in FIG. 12A.
FIG. 12B shows that an even better radiographic quality of newly formed bone grew in the defect using a coagulum containing calcium chloride and the fibrin sealant. See, Example 9, below, for details.
Figure 12B:

When implanted into a critical size rabbit ulnar defect, normal coagulum (no added calcium, no added fibrin-thrombin mixture) with added BMP-7 stimulated bone regeneration. However, as indicated by X-ray in FIGS. 9 and 10, the normal coagulum composition lacked the integrity and viscosity necessary to promote sufficient new bone formation to rebridge the defect. In particular, the consistency of the coagulum was insufficient to maintain a connection between two bone ends for the period of time needed to form bone throughout the defect length as indicated by X-ray at week 6 (FIG. 9) and at week 8 (FIG. 10). In another animal, the normal (unmodified) coagulum containing BMP-7 fell apart at an early time point, and only spots of mineralized tissue were observed by X-ray in the defect area at week 6 (FIG. 11A) and week 8 (FIG. 11B). In contrast, when a whole blood-derived coagulum device (WBCD) was formulated with calcium and fibrin sealant, the defect was rebridged. Addition of 1M $CaCl_2$ improved the viscosity of the coagulum such that the defect was filled with new bone at week 8 (see, FIG. 12A). The best radiographic quality of newly formed bone was observed at week 8 when the WBCD was prepared with both added calcium and added fibrin sealant (see, FIG. 12B).

Example 10

In Vitro Evaluation of Consistency and Viscosity of Coagulum Gel Formulations and Preferred Ranges of Component Ingredients Normal (unmodified) coagulum from whole blood remained compact and in one piece for three days. After that period of time, although in wet conditions, the coagulum did not maintain a continuous shape but fell apart into several piles of material. In contrast, when calcium chloride was added to whole blood at concentration in the range of 5 mM to 15 mM (or, in terms of calcium ion, alone, 1 mM-2.5 mM), the viscosity of the resulting coagulum gel was maintained for more than seven days. The coagulum gel also remained compact and in one cohesive piece. When the concentration of added calcium chloride was below 5 mM, the coagulum composition was similar to the normal unmodified coagulum fell apart. When the concentration of added calcium chloride exceeded 15 mM, the composition was too rigid and brittle and lost continuity after four days.

These results indicate that exogenously provided calcium chloride mixed with whole blood in a concentration range of 5 mM to 15 mM, inclusive, or, in terms of calcium ion alone, 1 mM to 2.5 mM, improves viscosity and consistency of the coagulum gel for effective use in treating bond defects.

Additional observations indicated that a preferred whole blood-derived coagulum device (WBCD) as described herein includes exogenously provided fibrin in the preferred range of 5 mg/mL to 10 mg/mL, inclusive, and exogenously provided thrombin in the preferred range of 0.5 mg/mL to 5 mg/mL, inclusive.

Evaluation of data from various studies as described above also indicated that a BMP or other osteogenic protein is preferably incorporated into a WBCD for use in treating bone defects in a preferred range of 50 µg/mL to 500 µg/mL.

All patents, applications, and publications cited in the above text are incorporated herein by reference.

Other variations and embodiments of the invention described herein will now be apparent to those of skill in the art without departing from the disclosure of the invention or the claims below.

The invention claimed is:
1. A whole blood-derived coagulum device (WBCD) for treating a bone defect in an individual comprising:
    (a) whole blood,
    (b) an osteogenic protein,
    (c) exogenously provided calcium chloride, and
    (d) optionally, an exogenously provided fibrin-thrombin mixture, wherein the exogenously provided calcium chloride is present in an amount that is effective to provide a homogeneous, cohesive, syringeable, injectable, and malleable coagulum gel that is capable of maintaining presence in a bone defect site for a period of time sufficient to promote growth of new bone to fill the defect or to rebridge bone ends of the defect.

2. The WBCD according to claim 1, wherein the whole blood is autologous whole blood drawn from the individual or whole blood that has been crossmatched with the individual.

3. The WBCD according to claim 1, wherein the osteogenic protein is an osteogenic BMP.

4. The WBCD according to claim 3, wherein the osteogenic BMP is selected from the group consisting of BMP-2, BMP-4, BMP-6, BMP-7, heterodimers thereof, and combinations thereof.

5. The WBCD according to claim 1, wherein the exogenously provided calcium chloride provides calcium ions at a concentration in the range of 1 mM to 2.5 mM, inclusive.

6. The WBCD according to any one of claims 1-4, wherein the exogenously provided calcium chloride is present in the range of 5 mM to 15 mM, inclusive.

7. The WBCD according to claim 1, wherein the exogenously provided fibrin-thrombin mixture is present.

8. The WBCD according to claim 7, wherein the exogenously provided fibrin-thrombin mixture provides fibrin in the range of 5 mg/mL to 10 mg/mL, inclusive.

9. The WBCD according to claim 7, wherein the exogenously provided fibrin-thrombin mixture provides thrombin in the range of 0.5 mg/mL to 5 mg/mL, inclusive.

10. The WBCD according to claim 7, wherein the exogenously provided fibrin-thrombin mixture is combined with the exogenously provided calcium chloride and the osteogenic protein to form a first mixture; followed by incubating the first mixture for at least 15 minutes; and thereafter the whole blood is added to the first mixture to form a second mixture, and the second mixture is incubated for about 20 minutes.

11. A method of treating a bone defect in an individual in need of treatment thereof comprising:
    1. preparing an osteogenic whole blood-derived coagulum device (WBCD) by the steps comprising:
        (a) combining:
            (i) whole blood,
            (ii) an osteogenic protein,
            (iii) exogenously provided calcium chloride, and
            (iv) optionally, a fibrin-thrombin mixture,
        (b) incubating the ingredients combined in step (a) until a mechanically stable coagulum is formed,
    wherein the exogenously provided calcium chloride is present at a concentration that is effective to provide a homogeneous, cohesive, syringeable, injectable, and malleable coagulum gel, and
    2. administering the WBCD of step 1 to the bone defect in the individual.

12. The method according to claim 11, wherein the whole blood is autologous whole blood drawn from the individual or whole blood that has been crossmatched with the individual.

13. The method according to claim 11, wherein the osteogenic protein is an osteogenic BMP.

14. The method according to claim 13, wherein the osteogenic BMP is selected from the group consisting of BMP-2, BMP-4, BMP-6, BMP-7, heterodimers thereof, and combinations thereof.

15. The method according to claim 11, wherein the exogenously provided calcium chloride provides calcium ions at a concentration in the range of 1 mM to 2.5 mM, inclusive.

16. The method according to any one of claims 11-14, wherein the exogenously provided calcium chloride is present in the range of 5 mM to 15 mM, inclusive.

17. The method according to claim 11, wherein the exogenously provided fibrin-thrombin mixture is present.

18. The method according to claim 17, wherein the exogenously provided fibrin-thrombin mixture provides fibrin in the range of 5 mg/mL to 10 mg/mL, inclusive.

19. The method according to claim 17, wherein the exogenously provided fibrin-thrombin mixture provides thrombin in the range of 0.5 mg/mL to 5 mg/mL, inclusive.

20. The method according to claim 17, wherein step (a) is carried out by preparing a first mixture by combining the exogenously provided fibrin-thrombin mixture, the exogenously provided calcium ion, and the osteogenic protein; followed by incubating the first mixture for at least 15 minutes; and thereafter adding the whole blood to the first mixture to form a second mixture, and incubating the second mixture for about 20 minutes.

21. The method according to claim 11, wherein the WBCD is administered by implantation into the bone defect.

22. The method according to claim 11, wherein the WBCD is administered by injection into the bone defect.

23. The method according to claim 11, wherein the bone defect is a fracture.

24. The method according to claim 11, wherein the individual has a metabolic bone disease.

25. The method according to claim 24, wherein the metabolic bone disease is selected from the group consisting of osteoporosis, osteopenia, and Paget's Disease.

26. A kit for preparing a whole blood-derived coagulum device (WBCD) for treating a bone defect comprising:
   1. a vial containing a lyophilized osteogenic BMP,
   2. a buffer for reconstituting the lyophilized BMP powder,
   3. a syringe and a needle for reconstituting the lyophilized BMP in the buffer,
   4. a vacutainer for collecting a patient's blood,
   5. a sterile solution of 1 M $CaCl_2$,
   6. a fibrin-thrombin mixture,
   7. a plastic, siliconized container for mixing whole blood with the reconstituted BMP,
   8. a spatula or a syringe for applying WBCD to bone ends during open surgery, and
   9. instructions for using the foregoing materials in the preparation of a WBCD in accordance with claim 1 using autologous or crossmatched blood.

* * * * *